United States Patent [19]

Gibson

[11] Patent Number: 4,963,132
[45] Date of Patent: Oct. 16, 1990

[54] CAPPED FLUIDIC CONNECTOR

[76] Inventor: Roger M. Gibson, 3446 NE. Kincaid, Topeka, Kans. 66617

[21] Appl. No.: 406,915

[22] Filed: Sep. 13, 1989

Related U.S. Application Data

[63] Continuation-in-part of Ser. No. 276,040, Nov. 11, 1988, abandoned.

[51] Int. Cl.⁵ ............................................. A61M 3/00
[52] U.S. Cl. ................................. 604/256; 604/283; 604/905; 285/331; 285/901
[58] Field of Search ............... 604/256, 283, 905, 380, 604/280; 285/331, 390, 901

[56] References Cited
U.S. PATENT DOCUMENTS 4,369,781  1/1983  Gailson et al. ..................... 604/905
4,636,204  1/1987  Christopherson et al. .......... 604/283

FOREIGN PATENT DOCUMENTS 0994631  8/1976  Canada ............................... 604/283

Primary Examiner—John D. Yasko
Assistant Examiner—Anthony M. Gutows
Attorney, Agent, or Firm—Litman, McMahon & Brown

[57] ABSTRACT

A capped fluidic connector is provided which includes a body with an inner tubular member having proximate and distal sections. A cap is hingedly connected to the body for covering the inner tubular member distal section. The inner tubular member proximate section is received within an outer tubular member proximate section. An application of the connector in an intravenous or intra-arterial fluid system is disclosed.

2 Claims, 2 Drawing Sheets

CAPPED FLUIDIC CONNECTOR

The present application is a continuation-in-part of U.S. Serial No. 07/276,040 on STOPCOCK ACCESS HINGED CAP, filed Nov. 11, 1988, now abandoned.

BACKGROUND OF THE INVENTION

1. Field of the Invention.

The present invention relates generally to fluidic connection devices, and in particular to a capped connector for facilitating aseptic fluid sampling and medication introduction in intravenous and intra-arterial systems.

2. Description of the Relevant Art.

Fluidic connectors are well known and a variety of different designs have heretofore been proposed to satisfy the objectives of various applications. Various mechanical connection procedures are available for fluidically interconnecting different fluid-conveying components such as tubing, valves, etc. These fluidic connecting techniques include friction fits, screw-threaded connections, adhesive connections, welded connections, etc. Closure devices, such as valves, are often provided in fluidic systems for controlling fluid flow volume and direction. For example, three-way stopcocks are commonly used in the medical field for controlling fluid flow in intravenous and intra-arterial systems. Such systems are commonly used in the medical field for introducing various fluids, including medication and nourishment. Other medical uses of such systems include pressure manometry (e.g. blood pressure testing) and rapid access to blood samples for testing. Such monitoring functions are particularly important in patients undergoing critical care. Reliable and accurate patient condition information can be extremely important to health care treating professionals.

A significant problem with such intravenous and intra-arterial systems is the risk of contamination and infection. This problem has been reported in the medical literature. See T. Shinozaki, R. Deane, J. Mazuzan, Jr., A. Hamel, D. Hazelton, *Bacterial Contamination of Arterial Lines*, 249 Journal of the American Medical Association p. 223 (Jan. 14, 1983) and K. Brosnan, A. Parham, B. Rutledge, D. Baker and J. Redding, *Stopcock Contamination*, American Journal of Nursing p. 320.

In intravenous and intra-arterial systems, sampling ports are often provided wherein blood samples can be withdrawn and/or blood pressure can be monitored. Such sampling ports can be provided in three-way stopcocks, which permit the selective closing of a fluid line while appropriate connections are made for sampling and monitoring. As reported by Shinozaki et al., supra, the sampling and monitoring ports are susceptible to bacteria entry. For example, such sampling ports are often provided with a removable closure cap. However, such caps are relatively small and thus susceptible to contamination if handled improperly. Due to their relatively small size, they also tend to be easily misplaced.

Other solutions include flushing the three-way valves and replacing the closure caps each time they are opened. However, such procedures tend to be labor intensive and expensive.

Heretofore there has not been available a capped fluidic connector with the advantages and features of the present invention.

SUMMARY OF THE INVENTION

In the practice of the present invention, a capped fluidic connector is provided which includes a body with proximate and distal ends and inner and outer tubular members. The inner tubular member includes a proximate end adapted for insertion in the sampling port of a three-way stopcock and a distal end adapted to receive a syringe nozzle. The outer tubular member partially surrounds the inner tubular member and can include female threading for threadably engaging the stopcock. A cap is hingedly connected to the body and can include a bore with a blind end for covering the inner tubular member distal end with the cap in a closed position thereof. In its open position the cap is spaced from the body to minimize the risk of contamination.

OBJECTS AND ADVANTAGES OF THE INVENTION

The principal objects and advantages of the present invention include: providing a capped fluidic connector; providing such a connector which includes a connecting tube which can be selectively covered and protected by a cap with the cap in a closed position thereof; providing such a connector which is particularly well adapted for a three-way stopcock sampling port in an intravenous or intra-arterial system; providing such a connector which promotes relatively aseptic conditions in blood monitoring and sampling procedures; providing such a connector which is economical to manufacture, efficient in operation, capable of a long operating life and particularly well adapted for the proposed usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

I. Introduction and Environment

Figure 1:
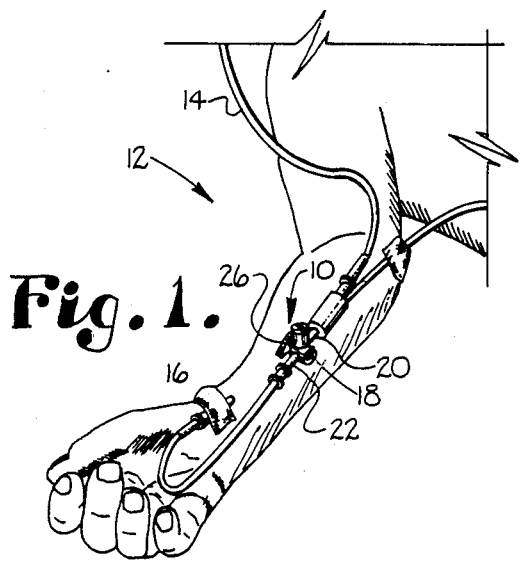
FIG. 1 is a perspective view of an intravenous or intra-arterial fluid system with a stopcock and a capped fluidic connector embodying the present invention shown attached to the stopcock.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience and reference only and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the structure being referred to. Said terminology will include the words specifically mentioned, derivatives thereof and words of similar import.

Referring to the drawings in more detail, the reference numeral 10 generally designates a capped fluidic connector embodying the present invention. Without limitation on the generality of useful applications of the connector 10, an exemplary application is shown in connection with an intravenous or intra-arterial (IV/IA) system 12 including IV/IA tubing 14 fluidically connected to a catheter 16 and a three-way stopcock 18. The IV/IA system 12 can be connected to monitoring equipment, flushing solutions, medications, etc. The three-way stopcock 18 includes proximate, distal and sampling ports 20, 22 and 24 which can be selectively interconnected by manipulating a valve lever 26.

The fluidic connector 10 generally comprises a connector body 28 (section II) and a connector cap 30 (section III).

II. Connector Body 28

The connector body 28 includes an inner tubular member 32 with proximate and distal ends 34, 36 and a coaxial bore 38 extending between the ends 32, 34. The proximate end or male insert port 34 has a tapered configuration and the distal end or female port 36 terminates at an externally male-threaded collar 40. Approximately intermediate its ends 34, 36, the inner tubular member 32 includes a tapered transition section 42 between a relatively narrow-diameter proximate section 44 and a larger-diameter distal section 46.

Figure 3:
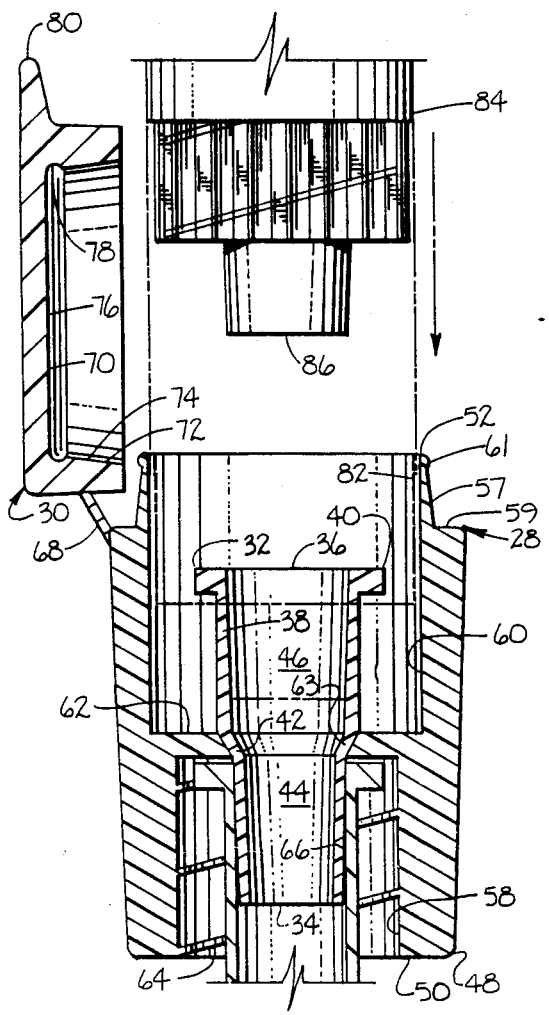
FIG. 3 is an enlarged, cross-sectional view of the capped fluidic connector with the cap shown in an open position thereof.

An outer tubular member 48 includes proximate and distal ends 50, 52 associated with proximate and distal sections 54, 56 having proximate and distal section bores 58, 60 separated by a plug 62 connected to and receiving the inner tubular member transition section 42 in a plug bore 63 The proximate section bore 58 has internal female threading 64 whereby the tubular member proximate sections 44, 54 form a combination tapered and threaded fluidic connector which is commonly referred to as a "Luer-Lock" connector, which in this exemplary application is adapted for connection to external male threads 25 on the sampling port 24 for securing the inner tubular member distal end 36 in a fluid-tight engagement in a bore 27 of the sampling port 24 (FIG. 3).

A proximate Luer-Lok connection is thus formed between the sampling port 24 and the body 28 by threadably twisting them together. The tapered configuration of the inner tubular member proximate end 32 facilitates a fluid-tight seal.

In proximity to the outer tubular member distal end 52, the distal section 56 includes a tapered throat 57 projecting outwardly from a shoulder 59 and terminating at an annular lip 61.

III. Connector Cap 30

Figure 2:
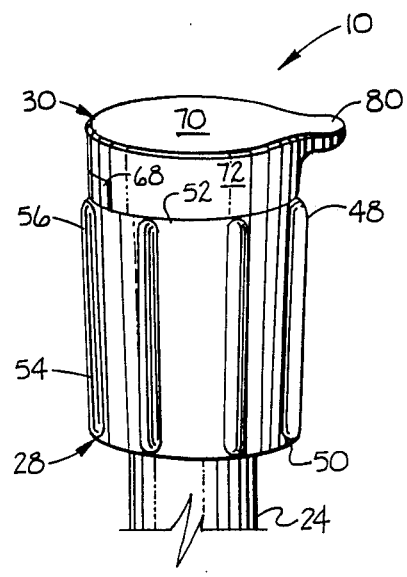
FIG. 2 is a perspective view of the capped fluidic connector with a cap thereof shown in a closed position.
Figure 4:
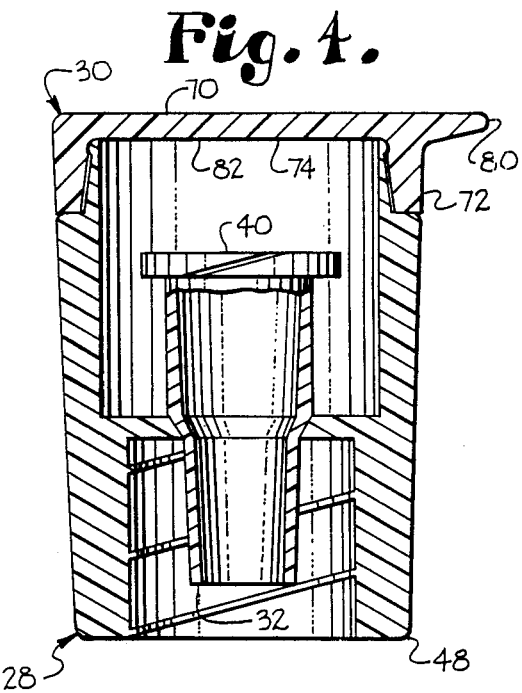
FIG. 4 is an enlarged, cross-sectional view of the capped fluidic connector with the cap shown in its closed position.

The connector cap 30 is hingedly connected to the outer tubular member distal section 56 by a hinge strap 68 and is thus movable between an open position (FIG. 3) and a closed position (FIGS. 2 and 4). The cap 30 includes a top 70 and a side wall 72 forming a relatively shallow cap bore 74 terminating at a closed end 76 with an annular groove 78. A finger tab 80 projects laterally from the top 70 diametrically opposite from the hinge strap 68.

IV. Operation

In operation, the connector 10 is adapted to provide a relatively aseptic connection in an IV/IA system 12, particularly with the sampling port 24 of the three-way stopcock 18. The proximate Luer-Lok connection 66 is formed between the sampling port 24 and the body 28 as described above. The cap 30 will normally be kept in its closed position (FIGS. 2 and 4) whereby a distal chamber 82 within the distal section bore 60 can be relatively hermetically sealed against contamination. For access to the IV/IA system 12 through the connector 10, the cap 30 is opened by engaging the finger tab 80 and pushing outwardly, thus releasing the snap connection between the lip 61 and the annular groove 78 and opening the distal chamber 82. A syringe 84 with a Luer-Lock type end 86 can be fluidically connected to the inner tubular member distal end 36 whereby a distal Luer-Lok connection is formed.

The outer tubular member distal section 56 shields the inner tubular member distal section 46 from contact with possible contamination sources such as the fingers of an attending physician or nurse. The syringe 84 can be used to draw a blood sample or administer a medication. Fluidic connections to other equipment, such as a blood pressure monitor, could be accomplished with the fluidic connector 10. It will be appreciated that the connector cap 30 can be opened and closed repeatedly. If necessary, the distal chamber 82 can be flushed with an antiseptic solution.

V. Alternative Embodiment

Figure 5:
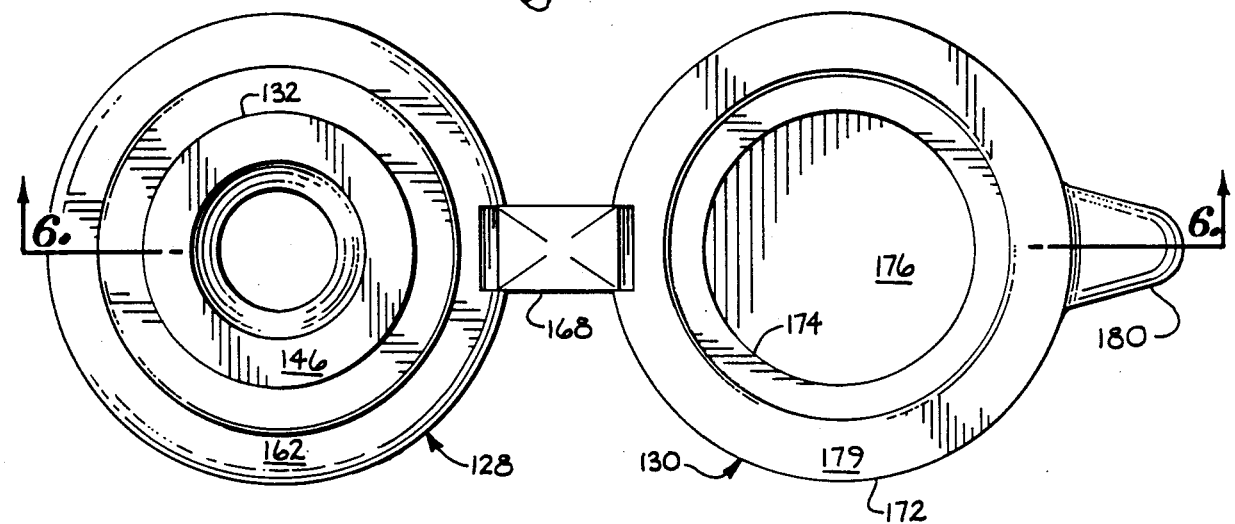
FIG. 5 is a top plan view of a capped fluidic connector comprising a modified embodiment of the present invention, shown with a cap thereof in its open position.
Figure 6:
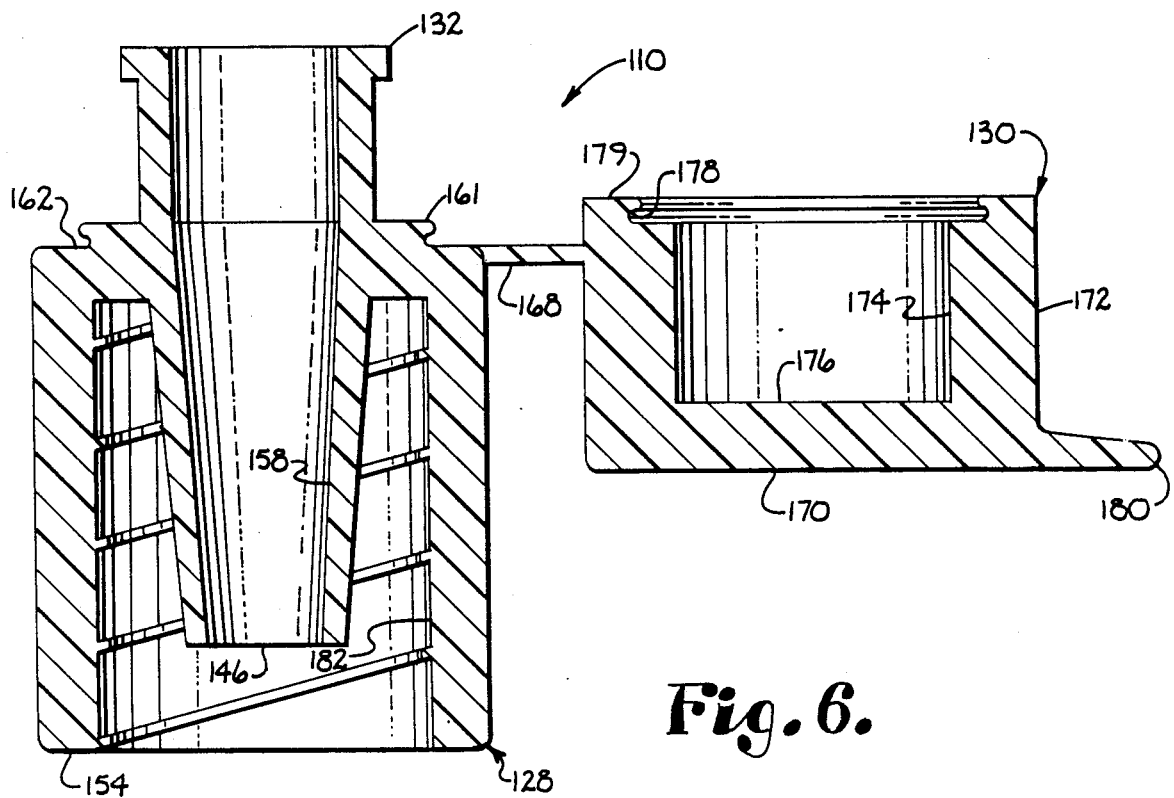
FIG. 6 is a cross-sectional view of the modified capped fluidic connector taken generally along line 6—6 in FIG. 5.

A capped fluidic connector 110 comprising an alternative or modified embodiment of the present invention is shown in FIGS. 5 and 6. The fluidic connector 110 includes a connector body 128 and an inner tubular member 132 with a configuration substantially similar to that of the inner tubular member 32, and includes an outer tubular member proximate section 134 with a configuration substantially similar to that of the outer tubular member proximate section 54. A distal section 146 of the inner tubular member 132 projects upwardly from a plug 162 which closes the end of a proximate section bore 158. The plug 162 includes an annular lip 161. A connector cap 130 includes a hinge strap 168 connected to the body 128 in proximity to the plug 162, a top 170, a side wall 172 and a cap bore 174 terminating at a closed end 176. An annular groove 178 is formed in the side wall 172 adjacent to a free edge 179 thereof. A finger tab 180 projects laterally from the cap top 170.

The cap bore 174 is designed to substantially contain the inner tubular member distal section 146 in a distal chamber 182 which is substantially hermetically sealed with the cap 130 in its closed position.

The hinge strap 168 can comprise "memory" type plastic whereby the cap 130, when released, automatically swings through an arc of about one hundred and eighty degrees to a position as shown in FIG. 5. In this open configuration, the cap 130 is positioned substantially out of the way to minimize the risk of contact and contamination. The exposed position of the inner tubular member distal section 146, with the cap 130 in its open position, facilitates antiseptic and antibacterial cleaning, especially in the event blood or other fluid overflows the connector 110.

The connectors 10 and 110 can comprise any suitable material constructed in any suitable manner. For example, plastic injection molding techniques can be utilized. The inner tubular member 32 could be formed as a separate piece for insertion through the bore 63 in the plug 62 as shown in FIG. 3. Alternatively, the entire connector, e.g. the embodiment designated 110, could be monolithically formed.

It is to be understood that while certain forms of the present invention have been illustrated and described herein, it is not to be limited to the specific forms or arrangement of parts described and shown.

What is claimed and desired to be secured by Letters Patent is as follows:

1. A capped fluid connector, which includes:
   (a) a connector body including:
      (1) an inner tubular member with a proximal tapered male end and a distal, externally-threaded end;
      (2) an inner tubular member bore extending coaxially therethrough and open at said proximal and said distal ends;
      (3) said inner tubular member including a proximal section terminating at said proximal end and a distal section terminating at said distal end;
      (4) an outer tubular member including a bore with internal, female threads, said bore being sealed and terminating at an annular plug with a distal face, said annular plug connected to said inner tubular member between the proximal and distal sections thereof, said outer tubular member having a proximal end, said outer tubular member bore being open at its proximal end;
      (5) said inner tubular member proximal end being located within said outer tubular member bore; and
      (6) said distal face including first connecting means;
      (7) said inner tubular member distal section projecting distally from said annular plug distal face; and
      (8) an annular clearance space between said outer tubular member and said inner tubular member proximal section within said outer tubular member bore; and
   (b) a cap including:
      (1) a closed top;
      (2) a sidewall extending from said top to a free, annular bottom edge;
      (3) a bore including a closed end adjacent to said top and an open end adjacent to said sidewall free edge, said bore being annularly surrounded by said sidewall;
      (4) said side wall including second connecting means adjacent said cap bore, said second connecting means comprising an annular groove open inwardly adjacent to said sidewall free edge;
      (5) a flexible hinge strap extending between said outer tubular member distal end and said sidewall;
      (6) a finger tab extending outwardly from said connector cap top;
      (7) said cap being movable through an arc of approximately 180° between an open position spaced outwardly from said connector body and a closed position with said first connecting means releasably received in said cap sidewall groove and said inner tubular member distal section received in said cap bore; and
      (8) said cap bore having a depth greater than a length of said inner tubular member distal section.

2. In combination with a three-way stopcock including an inlet port, an outlet port and a tubular, externally-threaded sampling port, the improvement of a capped connector, which comprises:
   (a) a connector body including:
      (1) an inner tubular member with a proximal tapered male end and a distal, externally-threaded end;
      (2) an inner tubular member bore extending coaxially therethrough and open at said proximal and said distal ends;
      (3) said inner tubular member including a proximal section terminating at said proximal end and a distal section terminating at said distal end;
      (4) an outer tubular member including a bore with internal, female threads, said bore being sealed and terminating at an annular plug with a distal face, said annular plug connected to said inner tubular member between the proximal and distal sections thereof, said outer tubular member having a proximal end, said outer tubular member bore being open at its proximal end;
      (5) said inner tubular member proximal end being located within said outer tubular member bore; and
      (6) said distal face including first connecting means;
      (7) said inner tubular member distal section projecting distally from said annular plug distal face; and
      (8) an annular clearance space between said outer tubular member and said inner tubular member proximal section within said outer tubular member bore; and
   (b) a cap including:
      (1) a closed top;
      (2) a sidewall extending from said top to a free, annular bottom edge;
      (3) a bore including a closed end adjacent to said top and an open end adjacent to said sidewall free edge, said bore being annularly surrounded by said sidewall;
      (4) said side wall including second connecting means adjacent said cap bore, said second connecting means comprising an annular groove open inwardly adjacent to said sidewall free edge;

(5) a flexible hinge strap extending between said outer tubular member distal end and said sidewall;
(6) a finger tab extending outwardly from said connector cap top;
(7) said cap being movable through an arc of approximately 180° between an open position spaced outwardly from said connector body and a closed position with said first connecting means releasably received in said cap sidewall groove and said inner tubular member distal section received in said cap bore; and
(8) said cap bore having a depth greater than a length of said inner tubular member distal section.

* * * * *